US010806905B2

(12) United States Patent
Asmus

(10) Patent No.: US 10,806,905 B2
(45) Date of Patent: Oct. 20, 2020

(54) REFORMABLE GUIDEWIRE TIP

(71) Applicant: Cardiovascular Systems, Inc., New Brighton, MN (US)

(72) Inventor: Bruce H. Asmus, Minnetonka, MN (US)

(73) Assignee: Cardiovascular Systems, Inc., New Brighton, MN (US)

( * ) Notice: Subject to any disclaimer, the term of this patent is extended or adjusted under 35 U.S.C. 154(b) by 722 days.

(21) Appl. No.: 14/816,367

(22) Filed: Aug. 3, 2015

(65) Prior Publication Data

US 2016/0038719 A1 Feb. 11, 2016

Related U.S. Application Data

(60) Provisional application No. 62/033,346, filed on Aug. 5, 2014.

(51) Int. Cl.
*A61M 25/09* (2006.01)
*A61B 17/3207* (2006.01)
(Continued)

(52) U.S. Cl.
CPC ......... *A61M 25/09* (2013.01); *A61B 17/3207* (2013.01); *A61B 17/320758* (2013.01); *A61B 2017/00867* (2013.01); *A61B 2017/00871* (2013.01); *A61B 2017/22042* (2013.01); *A61B 2017/320004* (2013.01); *A61B 2017/320766* (2013.01); *A61M 2025/09083* (2013.01);
(Continued)

(58) Field of Classification Search
CPC ............... A61M 25/09; A61B 17/3207; A61B 17/320758
USPC ........................................................ 600/585
See application file for complete search history.

(56) References Cited

U.S. PATENT DOCUMENTS 4,763,647 A * 8/1988 Gambale ......... A61M 25/09033 600/434
5,065,769 A 11/1991 de Toledo
(Continued)

FOREIGN PATENT DOCUMENTS

CN 103281974 A 9/2013
CN 103957825 A 7/2014
(Continued)

OTHER PUBLICATIONS

International Preliminary Report on Patentability dated Feb. 16, 2017 for PCT Application No. PCT/US2015/043521, filed Aug. 4, 2015.

*Primary Examiner* — Daniel L Cerioni
(74) *Attorney, Agent, or Firm* — Barnes & Thornburg LLP; Jeffrey R. Stone

(57) ABSTRACT

Devices and methods for providing an elastically deforming guidewire tip, capable of withstanding the extreme forces of high-speed rotational atherectomy, in particular orbital motion induced by an eccentric abrasive head, are disclosed. In certain embodiments, the reformable tip comprises an inner nitinol support coil, wherein the reformable tip may be attached to a larger proximal core for improved kink resistance and support for delivering adjunctive devices. In other embodiments, an inner nitinol support coil may be wrapped with a braided coil and/or a polymer sleeve. The resulting tip is more flexible with reduced risk of perforation than known guidewire tips.

17 Claims, 2 Drawing Sheets

200
110 118 112 202
116
106

(51) Int. Cl.
*A61B 17/00* (2006.01)
*A61B 17/32* (2006.01)
*A61B 17/22* (2006.01)

(52) U.S. Cl.
CPC ............. *A61M 2025/09091* (2013.01); *A61M 2025/09175* (2013.01); *A61M 2205/0266* (2013.01)

(56) References Cited

U.S. PATENT DOCUMENTS 5,312,427 A * 5/1994 Shturman .......... A61B 17/3207 606/159
5,376,083 A * 12/1994 Mische ................. A61M 25/09 600/585
5,596,996 A * 1/1997 Johanson .............. A61M 25/09 600/434
5,827,201 A * 10/1998 Samson ................ A61M 25/09 600/585
5,836,868 A * 11/1998 Ressemann .... A61B 17/320725 606/159
2005/0065456 A1* 3/2005 Eskuri ................... A61M 25/09 600/585
2006/0198976 A1* 9/2006 Trapp ...................... A61L 29/04 428/36.9
2009/0018566 A1* 1/2009 Escudero ......... A61B 17/32075 606/159
2010/0318065 A1* 12/2010 Miyata .................. A61M 25/09 604/526
2011/0060316 A1* 3/2011 DiCarlo ................ A61M 25/09 604/529
2012/0172905 A1* 7/2012 Lee Shee ........... A61B 17/1671 606/180
2013/0096587 A1* 4/2013 Smith ............ A61B 17/320758 606/159

FOREIGN PATENT DOCUMENTS

EP 2 263 736 12/2010
JP 63181774 A 7/1988
JP H11262676 9/1999
JP 2006-516424 7/2006
JP 2007514458 A 6/2007

* cited by examiner

REFORMABLE GUIDEWIRE TIP

CROSS-REFERENCE TO RELATED APPLICATIONS

This application claims the benefit of U.S. Provisional Application No. 62/033,346, filed Aug. 5, 2014, the entirety of which is hereby incorporated by reference.

STATEMENT REGARDING FEDERALLY SPONSORED RESEARCH OR DEVELOPMENT

Not Applicable

BACKGROUND OF THE INVENTION

Field of the Invention

The disclosure relates to devices and methods using guidewires, for example intravascular procedures, e.g., removing tissue from body passageways, such as removal of atherosclerotic plaque from arteries with, e.g., a rotational atherectomy device. More specifically, the disclosure provides a guidewire tip that is reformable and, therefore, resistant to damaging deformation.

Description of the Related Art

A variety of techniques and instruments have been developed for use in the removal or repair of tissue in arteries and similar body passageways. A frequent objective of such techniques and instruments is the removal of atherosclerotic plaque in a patient's arteries. Atherosclerosis is characterized by the buildup of fatty deposits (atheromas) in the intimal layer (i.e., under the endothelium) of a patient's blood vessels. Very often over time what initially is deposited as relatively soft, cholesterol-rich atheromatous material hardens into a calcified atherosclerotic plaque. Such atheromas restrict the flow of blood, and therefore often are referred to as stenotic lesions or stenoses, the blocking material being referred to as stenotic material. If left untreated, such stenoses can cause angina, hypertension, myocardial infarction, strokes and the like.

Several kinds of atherectomy devices have been developed for attempting to remove some or all of such stenotic material. In one type of device, such as that shown in U.S. Pat. No. 4,990,134 (Auth), a rotating burr covered with an abrasive cutting material, such as diamond grit (diamond particles or dust), is carried at the distal end of a flexible, rotatable drive shaft.

U.S. Pat. No. 5,314,438 (Shturman) shows another atherectomy device having a rotatable drive shaft with a section of the drive shaft having an enlarged diameter, at least a segment of this enlarged diameter section being covered with an abrasive material to define an abrasive segment of the drive shaft. When rotated at high speeds, the abrasive segment is capable of removing stenotic tissue from an artery.

Intravascular procedures, for example and without limitation, rotational atherectomy systems, require a guidewire. Known guidewires used in traversing blood vessels may bend and may ultimately deform permanently during a procedure and, therefore, become unusuable as well as potentially harmful to the patient. In this case, deformed guidewires must be removed and a replacement guidewire threaded to the region of interest within a patient's vasculature.

Particularly, in a high-speed orbital atherectomy system, created by high-speed rotation of an eccentric abrasive drive shaft element, such as marketed by Cardiovascular Systems, Inc., ("CSI"), the stress forces and resulting fatigue on the guidewire can be permanently damaging. Primarily, in the case of CSI's systems, the guidewire is used in a high-speed atherectomy device that involves an eccentric abrasive element, having a center of mass that is radially positioned outwardly away from the rotational axis of the drive shaft to which the eccentric abrasive element is attached. High-speed rotation of this eccentric abrasive element thus results in orbital motion, i.e., a working diameter for the abrasive element that is larger than its resting diameter. Stated differently, the rotating eccentric abrasive element and surrounding portions of the rotational drive shaft to which it is attached experience radial excursions away from the resting rotational axis of the drive shaft. This concept is described fully in U.S. Pat. No. 6,494,890, the contents of which are hereby incorporated by reference in its entirety. This radial, or orbital, motion, causes high levels of forces to be transferred to the guidewire where damage may occur, even in cases where the guidewire uses a nitinol core for the guidewire tip.

Accordingly, there exists a need for a guidewire that comprises a tip that is capable of elastic deformation caused by very high forces as described supra, but also capable of returning and recovering back to the original undeformed shape and structure.

BRIEF SUMMARY OF THE INVENTION

Devices and methods for providing an elastically deforming guidewire tip, capable of withstanding the extreme forces of, for example and without limitation, high-speed rotational atherectomy, in particular orbital motion induced by an eccentric abrasive head, are disclosed. The guidewire tip may be used in other procedures and may be a standalone device. In certain embodiments, the reformable tip comprises an inner nitinol support coil, wherein the reformable tip may be attached to a larger proximal core for improved kink resistance and support for delivering adjunctive devices. In other embodiments, an inner support ribbon coil, constructed of a shape-memory material, e.g., Nitinol, may be wrapped with a braided coil and/or a polymer sleeve. In other embodiments, the braided coil and/or polymer sleeve may serve the same function as the inner support ribbon coil and replace the inner support ribbon coil. The resulting tip is more flexible with reduced risk of perforation than known guidewire tips.

DETAILED DESCRIPTION OF THE INVENTION

Figure 1A:
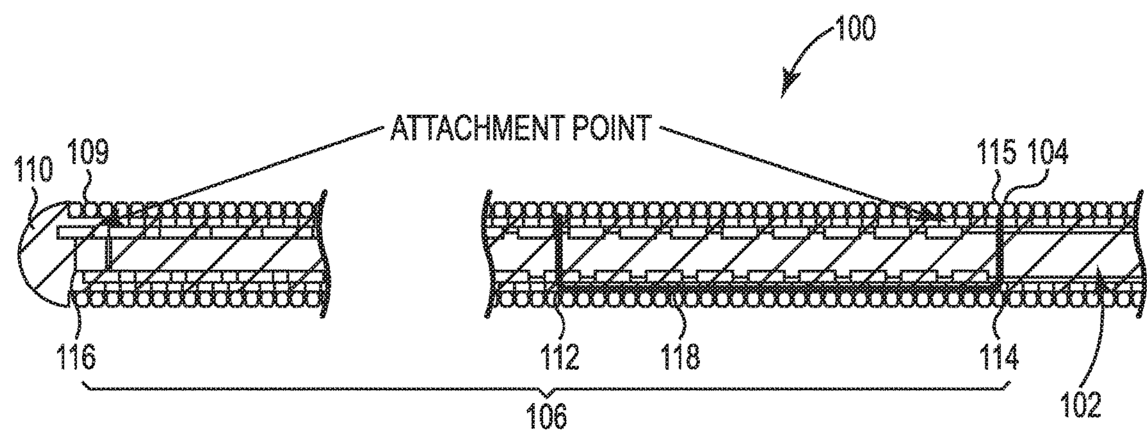
FIG. 1A illustrates one embodiment of the present invention in cross-sectional and cutaway view.

In the following detailed description of the various embodiments illustrated in the appended figures, like components and elements are identified using like reference numerals.

FIG. 1A illustrates one embodiment of the present invention, comprising a cutaway view of a guidewire 100 with a core 102 extending proximally to a proximal end available for manipulation by the operator (not shown but is as well-known to the skilled artisan). Core 102 further comprises a distal end 104. Reformable tip 106 comprises a distal end 109, distal end comprising a distal tip 110 disposed thereon and which may be radiopaque. Reformable tip 106 further comprises a flattened shape memory material support coil 112, support coil 112 comprising a proximal end 114 and a distal end 116, proximal end 114 in attached disposition with the distal end of core 109 at attachment point 115. Surrounding at least part of the core 102 and the flattened material support coil 112 is a spring coil 118, at least a portion of which may be radiopaque. In some embodiments, core 102 may comprise an outer diameter that is smaller than an inner diameter of support coil 112 at attachment point 115. Alternatively, core 102 may comprise an outer diameter that is larger than the inner diameter of support coil 112 at attachment point 115. Still more alternatively, core 102 may comprise an outer diameter that is larger than the outer diameter of support coil 112 at attachment point 115.

Figure 1B:
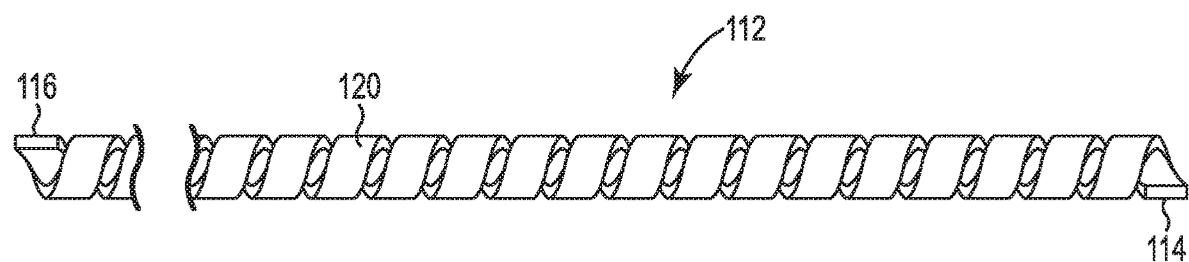
FIG. 1B illustrates one embodiment of a shape-memory ribbon coil of the present invention in side view.

FIG. 1B illustrates the flattened material support coil 112 in closer detail. As can be seen, the shape memory material has been flattened to a desired thickness and cut to a desired width. Then, the shape memory material, thus cut, has been rolled and set or trained at high temperatures into the coiled structure of FIG. 1B. One embodiment of the coil 112 comprises the coil material having a thickness of 0.00175 inches, with a nominal inner diameter after shape setting in the coil form of approximately 0.0058 inches, though the skilled artisan will recognize the varying dimensions of the coil material, including the pitch, each such equivalent dimensional combination is within the scope of the present invention. Coil 112 is illustrated as comprising a left-hand winding, though a right-hand winding may also be used. In the case of the illustrated left-hand winding, the spring coil 118 which surrounds the coil 112, comprises an opposite winding, i.e., a right-hand winding. Again, the skilled artisan will recognize the equivalence of the winding directions for these elements, each combination is within the scope of the present invention.

Figure 2A:
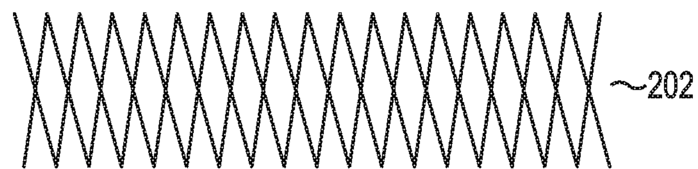
FIG. 2A illustrates one embodiment of a braided coil of the present invention in side view.
Figure 2B:
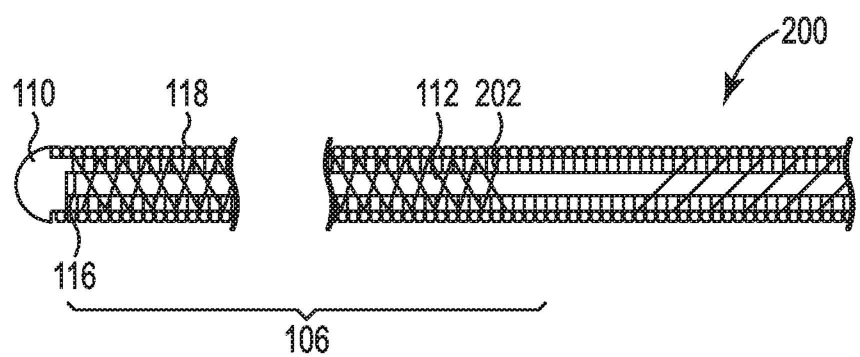
FIG. 2B illustrates one embodiment of the present invention in cross-sectional and cutaway view.

Turning now to FIGS. 2A and 2B, an alternate embodiment of the inventive guidewire 200 is illustrated. This embodiment is identical to that of FIGS. 1A and 1B except that a loose braid 202 comprising stainless steel, a polymer or a shape memory material, or a combination thereof, is provided along the reformable tip 106 from the distal end of the support coil 109 to the proximal end of the support coil 114. The loose braid 202 may be applied around external surface 120 of the support coil 112 with the spring coil 118 surrounding the loose braid 202 and support coil 112. Alternatively, the loose braid 202 may be disposed between wire turns of the support coil 112. Still more alternatively, the loose braid 202 may be employed in guidewire 200 instead of the support coil 112, serving the same function as the support coil 112 embodiment.

Figure 3:
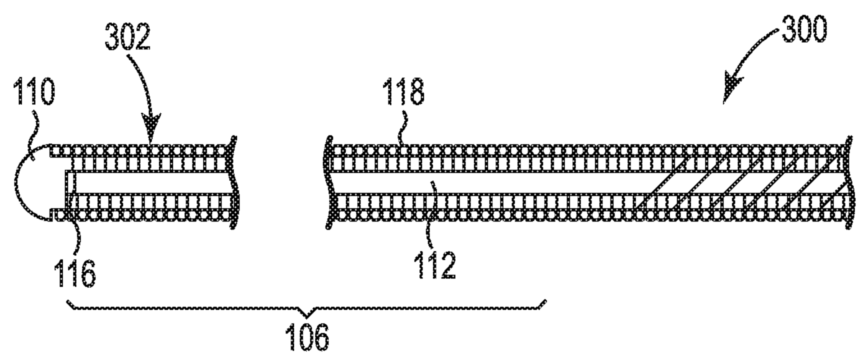
FIG. 3 illustrates one embodiment of the present invention in cross-sectional and cutaway view.

FIG. 3 illustrates yet another embodiment of a guidewire 300 of the present invention. In this embodiment, which is identical to that of FIGS. 2A and 2B except that, instead of the loose braid 202, a polymer sleeve 302 is provided along and the reformable tip 106. Polymer sleeve 302 may comprise nylon, pebax, fluorinated ethylene propylene (FEP), polytetrafluoroethylene (PTFE) and/or perfluoroalkoxy polymer resin (PFA). In this embodiment, the polymer sleeve 302 may cover the external surface 120 of the support coil 112, with the spring coil 118 surrounding the support coil 112 and polymer sleeve 302. Alternatively, the polymer sleeve 302 may be disposed over the wire turns of the support coil 112 along the corresponding length of the reformable tip 106. Still more alternatively, the wire turns of support coil 112 may be embedded within a polymer sleeve. Still more alternatively, the polymer sleeve 302 may be employed in guidewire 300 instead of the support coil 112, serving the same function as the embodiment having the support coil 112.

Various embodiments of the inventive guidewire and reformable tip thereof may comprise a hydrophilic coating along at least the reformable tip 106 and in certain embodiments along the length of the guidewire, and may further comprise a coating of silicone over the hydrophilic coating and/or along the length of the guidewire. This coating treatment assists and eases positioning of the guidewire as well as provides increased deliverability of adjunctive devices along the positioned guidewire.

The various embodiments of the guidewire having a reformable tip as described herein result in a reformable tip that is more flexible than known guidewire tips, which greatly reduces the risk of perforation during an intravascular procedure.

The descriptions of the embodiments and their applications as set forth herein should be construed as illustrative, and are not intended to limit the scope of the disclosure. Features of various embodiments may be combined with other embodiments and/or features thereof within the metes and bounds of the disclosure. Upon study of this disclosure, variations and modifications of the embodiments disclosed herein are possible, and practical alternatives to and equivalents of the various elements of the embodiments will be understood by and become apparent to those of ordinary skill in the art. Such variations and modifications of the embodiments disclosed herein may be made without departing from the scope and spirit of the invention. Therefore, all alternatives, variations, modifications, etc., as may become to one of ordinary skill in the art are considered as being within the metes and bounds of the instant disclosure.

What is claimed is:

1. A guidewire, comprising:

a core having a proximal end and a distal end and at least partially surrounded by a spring coil comprising wire turns;

a reformable tip having a distal end, a distal tip disposed on the distal end, and a proximal end, wherein the proximal end of the reformable tip and the distal end of the core are attached, the reformable tip further comprising a support coil formed from a flattened shape memory material and comprising an external surface, an inner diameter, a non-tapering outer diameter and a pitch, the support coil further comprising a proximal end and a distal end, the distal end of the support coil in communication with the distal tip and the proximal end of the support coil in attached communication with the distal end of the core such that the core does not extend distally of the proximal end of the support coil, wherein the spring coil further surrounds an external surface of the support coil; and a loose braid surrounding the external surface of the support coil.

2. The guidewire of claim 1, wherein the shape memory material comprises nitinol.

3. The guidewire of claim 1, wherein the loose braid is made of one or more of the group consisting of: stainless steel, nitinol, and a polymer.

4. The guidewire of claim 1, wherein the loose braid is made of one or more of the group consisting of: stainless steel, nitinol, and a polymer.

5. The guidewire of claim 1, further comprising a polymer sleeve surrounding the external surface of the support coil.

6. The guidewire of claim 5, wherein the polymer sleeve is made of one or more of the group consisting of: nylon, pebax, fluorinated ethylene propylene (FEP), polytetrafluoroethylene (PTFE) and perfluoroalkoxy polymer resin (PFA).

7. The guidewire of claim 1, further comprising a polymer sleeve surrounding the spring coil.

8. The guidewire of claim 7, wherein the polymer sleeve is made of one or more of the group consisting of: nylon, pebax, fluorinated ethylene propylene (FEP), polytetrafluoroethylene (PTFE) and perfluoroalkoxy polymer resin (PFA).

9. The guidewire of claim 1, further comprising the wire turns of the guidewire embedded within a polymer sleeve.

10. The guidewire of claim 9, wherein the polymer sleeve is made of one or more of the group consisting of: nylon, pebax, fluorinated ethylene propylene (FEP), polytetrafluoroethylene (PTFE) and perfluoroalkoxy polymer resin (PFA).

11. A guidewire, comprising:

a core having a proximal end and a distal end and at least partially surrounded by a spring coil comprising wire turns;

a reformable tip having a distal end, a distal tip disposed on the distal end, and a proximal end, wherein the proximal end of the reformable tip and the distal end of the core are attached, the reformable tip further comprising a support coil formed from nitinol and comprising an external surface, an inner diameter, a non-tapering outer diameter and a pitch, the support coil further comprising a proximal end and a distal end, the distal end of the support coil in communication with the distal tip and the proximal end of the support coil in attached communication with the distal end of the core such that the core does not extend distally of the proximal end of the support coil, wherein the spring coil further surrounds an external surface of the support coil; and a loose braid surrounding the external surface of the support coil.

12. The guidewire of claim 11, wherein the loose braid is made of one or more of the group consisting of: stainless steel, nitinol, and a polymer.

13. The guidewire of claim 11, wherein the loose braid is made of one or more of the group consisting of: stainless steel, nitinol, and a polymer.

14. The guidewire of claim 11, further comprising a polymer sleeve surrounding the external surface of the support coil.

15. The guidewire of claim 14, wherein the polymer sleeve is made of one or more of the group consisting of: nylon, pebax, fluorinated ethylene propylene (FEP), polytetrafluoroethylene (PTFE) and perfluoroalkoxy polymer resin (PFA).

16. The guidewire of claim 11, further comprising a polymer sleeve surrounding the spring coil.

17. The guidewire of claim 16, wherein the polymer sleeve is made of one or more of the group consisting of: nylon, pebax, fluorinated ethylene propylene (FEP), polytetrafluoroethylene (PTFE) and perfluoroalkoxy polymer resin (PFA).

* * * * *